(12) United States Patent
Ludwig et al.

(10) Patent No.: US 10,935,507 B2
(45) Date of Patent: Mar. 2, 2021

(54) THERMAL CONDUCTIVITY DETECTOR FOR GAS MIXTURES HAVING AT LEAST THREE COMPONENTS

(71) Applicant: Siemens Aktiengesellschaft, Munich (DE)

(72) Inventors: Michael Ludwig, Karlsruhe (DE); Günter Marcaux, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 148 days.

(21) Appl. No.: 16/338,132

(22) PCT Filed: Sep. 29, 2017

(86) PCT No.: PCT/EP2017/074871
§ 371 (c)(1),
(2) Date: Mar. 29, 2019

(87) PCT Pub. No.: WO2018/060479
PCT Pub. Date: Apr. 5, 2018

(65) Prior Publication Data
US 2020/0049681 A1 Feb. 13, 2020

(30) Foreign Application Priority Data
Sep. 30, 2016 (EP) .................... 16191950

(51) Int. Cl.
*G01N 25/18* (2006.01)
*G01N 33/00* (2006.01)
(Continued)

(52) U.S. Cl.
CPC ............. *G01N 25/18* (2013.01); *G01K 13/02* (2013.01); *G01N 33/0073* (2013.01);
(Continued)

(58) Field of Classification Search
CPC ........ G01N 25/18; G01N 25/22; G01N 25/40; G01N 25/48; G01N 33/0062;
(Continued)

(56) References Cited

U.S. PATENT DOCUMENTS 4,902,138 A 2/1990 Goeldner et al.
6,338,271 B1 1/2002 Stark
(Continued)

FOREIGN PATENT DOCUMENTS

DE 2505669 9/1976
DE 19909469 9/2000
(Continued)

OTHER PUBLICATIONS

S. Udina et al.: "A micromachined thermoelectric sensor for natural gas analysis: Thermal model and experimental results", Sensors and Actuators B 134 (2008) 551-558; Multivariate calibration results, Sensors and Actuators B: Chemical: International Journal Devoted to Research and Development of Physical and Chemical Transducers, Elsevier BV, NL, vol. 166, pp. 338-348, XP028486933, ISSN: 0925-4005, DOI: 10.1016/J.SNB.2011.11.086, found on Mar. 1, 2012; The whole document.

(Continued)

*Primary Examiner* — Benjamin R Schmitt
(74) *Attorney, Agent, or Firm* — Cozen O'Connor

(57) ABSTRACT

A gas analyzer for a gas mixture with at least three components includes a channel guiding the gas mixture, a thermoelement probe with a measuring point in the interior of the channel and a cold junction in thermal contact with the channel wall, a control device for pulsed activation of the thermoelement probe, a measuring device for measuring voltage at the cold junction in pauses between current pulses, and an evaluation device for determining temperature differences and calculating the ratio of the components (Continued)

of the gas mixture from temperature difference values determined at different time instant pauses, wherein the control device generates current pulses with at least two different energy contents and the temperature difference values at the first time instant in the pause after a current pulse with a higher energy content and used for the calculation is higher than with a current pulse with a lower energy content.

8 Claims, 2 Drawing Sheets

(51) Int. Cl.
*G01K 13/02* (2021.01)
*G01F 1/688* (2006.01)

(52) U.S. Cl.
CPC ...... *G01F 1/6888* (2013.01); *G01K 2013/024* (2013.01); *G01N 33/0062* (2013.01)

(58) Field of Classification Search
CPC ............... G01N 33/0073; G01K 13/02; G01K 2013/024; G01F 1/6888
USPC .................................. 73/25.01, 25.03, 25.05
See application file for complete search history.

(56) References Cited

U.S. PATENT DOCUMENTS

| 6,378,365 | B1 | 4/2002 | Tu |
| 2006/0220164 | A1 | 10/2006 | Murthy et al. |
| 2007/0209977 | A1 | 9/2007 | Wilf et al. |
| 2007/0241093 | A1 | 10/2007 | Von Waldkirch et al. |
| 2011/0252868 | A1 | 10/2011 | Döring et al. |
| 2016/0216227 | A1* | 7/2016 | Boni ................. G01N 33/004 |

FOREIGN PATENT DOCUMENTS

| DE | 102005033867 | 1/2007 |
| EP | 0187723 | 7/1986 |
| EP | 0285833 | 10/1988 |
| EP | 0698786 | 2/1996 |

OTHER PUBLICATIONS

G. De Graaf et al.: "Surface-micromachined thermal conductivity detectors for gas sensing", Proc. of the IEEE International Instrumentation and Measurement Technology Conference (I2MTC), Graz, May 13-16, 2012, 1861-1864; 2012.

* cited by examiner

THERMAL CONDUCTIVITY DETECTOR FOR GAS MIXTURES HAVING AT LEAST THREE COMPONENTS

CROSS-REFERENCE TO RELATED APPLICATIONS

This is a U.S. national stage of application No. PCT/EP2017/074871 filed Sep. 29, 2017. Priority is claimed on EP Application No. 16191950 filed Sep. 30, 2016, the content of which is incorporated herein by reference in its entirety.

BACKGROUND OF THE INVENTION

1. Field of the Invention

The invention relates to a heat conductivity detector.

2. Description of the Related Art

Thermoelectric heat conductivity detectors or flow sensors with a heating element and at least one thermoelement for measuring the temperature are known, therefore e.g. from: G. De Graaf et al.: "Surface-micromachined thermal conductivity detectors for gas sensing", Proc. of the IEEE International Instrumentation and Measurement Technology Conference (I2MTC), Graz, 13-16 May 2012, 1861-1864; S. Udina et al.: "A micromachined thermoelectric sensor for natural gas analysis: Thermal model and experimental results", Sensors and Actuators B 134 (2008) 551-558; DE 10 2005 033 867 A1; US 2006/0220164 A1; U.S. Pat. No. 6,378,365 B1; and US 2007/241093 A1.

EP 0 187 723 A2 or DE 199 09 469 C1 also discloses heating the thermoelement simultaneously (Peltier-effect) and using it to measure the temperature (Seebeck effect). The heating is performed using alternating current.

Finally, US 2007/209977 A1 discloses a flow meter (anemometer), in which a thermoelement is arranged in a flow path and around which a fluid (here a liquid) circulates. The thermoelement is heated up in a pulsed manner, by being periodically connected to a power supply source via a switch. The thermoelement cools down between the heat pulses, where the time constant of the cooling is dependent on the flow speed of the fluid. In the cooling phase, the temperature of the thermoelement is measured at two different points in time by measuring its electrical voltage. The flow speed of the fluid is calculated from the two obtained temperature values. The known flow meter is used to evaluate the performance of reverse osmosis membranes and can be supplemented by a measuring cell for measuring the electrical performance of the liquid.

As specified, e.g., in the afore-cited publication by S. Udina et al., the thermoelectric heat conductivity detector can be a component part of a gas analyzer for the purpose of determining the ratio of the components of a binary gas mixture.

It is furthermore known, e.g., from EP 0 285 833 A2 to operate a conventional heat conductivity detector with resistive elements at N−1 different temperatures, in order to analyze gas mixtures with N-components. However, it is necessary here to adjust the different heating temperatures very precisely. Furthermore, the thermal time constant of the heat conductivity detector must be sufficiently small to be able to rapidly adjust the different temperatures.

SUMMARY OF THE INVENTION

In view of the foregoing, it is therefore an object of the invention to provide a heat conductivity detector that enables a very rapid and precise analysis of ternary or multiple gas mixtures in a very simple way.

This and other objects and advantages are achieved in accordance with the invention by a gas analyzer for a gas mixture with at least three components, which has a channel guiding the gas mixture, a thermoelement probe with a measuring point in the interior of the channel and a cold junction in thermal contact with the wall of the channel, a control device, which is configured to provide pulsed activation of the thermoelement probe with current pulses, a measuring device, which is configured to measure the voltage at the cold junction of the thermoelement probe in the pauses between the current pulses, and an evaluation device, which is configured to determine the temperature difference between the measuring point and the cold junction from the measured voltage and configured to calculate the ratio of the components of the gas mixture from temperature difference values determined at at least two different time instants in each pause, where the control device is also configured to generate current pulses with at least two different energy contents, and where the evaluation device is also configured to capture a higher temperature difference value in the pause after a current pulse with a higher energy content at the first time instant and to use the captured higher temperature difference value for the calculation than after a current pulse with a lower energy content.

The measuring point, i.e., the hot connecting point of the thermoelement probe is therefore heated significantly to differing degrees during the course of the pulsed activation, so that temperature differences of differing degrees between the hot measuring point of the thermoelement probe and the comparatively cold wall of the channel guiding the gas mixture are present at least in the initial phases of the pauses following the different current pulses, where the temperature differences are measured via a thermoelement probe.

Advantageously, this actually does not depend on the accuracy of the heating temperature of the thermoelement probe, because the temperature difference or its course is only measured after the thermoelement probe has been heated in the pauses between the current pulses. The only decisive point is that the temperature difference value captured initially in the pause after a current pulse with a larger energy content is higher than the temperature difference value captured initially in the case of a current pulse with a smaller energy content. This is always then the case if the time instants for determining the temperature difference values are fixed at predetermined time intervals at the end of the respectively preceding current pulse, because with a more intensive heating of the thermoelement probe after a predetermined time following the heating process has elapsed, a higher temperature is present, than in the case of a lower heating after the same time.

On the one hand, the temperature difference between the measuring point of the thermoelement probe and the wall of the channel guiding the gas mixture subsides exponentially after each current pulse as a function of the heat conductivity of the gas mixture. On the other hand, the heat conductivity of gases is generally a function of the gas temperature and this function is different for different gases. As a result, at least three different components can be quantitatively determined relative to one another in the gas mixture based on at least two different courses of the temperature difference subsiding in the pauses between the current pulses. Here, the at least two different courses of the subsiding temperature difference are produced by heating the measuring points to differing levels with current pulses with a different energy content.

In order to obtain the exponentially subsiding course of the temperature difference, it is sufficient to determine at least two temperature difference values at at least two different time instants in each pause. As already mentioned above, these time instants can be fixed at predetermined intervals at the end of the respectively preceding current pulse.

Alternatively, at least two different temperature difference values can be predetermined and the time instants at which these predetermined temperature difference values are reached are determined in the exponentially subsiding course of the temperature difference. The intervals between the determined time instants at the end of the respectively preceding current pulse are then used to calculate the ratio of the components in the gas mixture.

As already mentioned above, it does not depend on the accuracy of the respective heating temperature of the thermoelement probe. Consequently, it also plays no role in how the current pulses are generated. The current pulses with different energy contents can therefore have different pulse heights and/or different pulse widths. If the energy content of the current pulse is set exclusively by way of its width or duration, the control device, which generates the current pulses, therefore does not need to provide different electrical voltages.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

To further explain the invention, reference is made below to the figures in the drawings, in which.

DETAILED DESCRIPTION OF THE EXEMPLARY EMBODIMENTS

Figure 1:
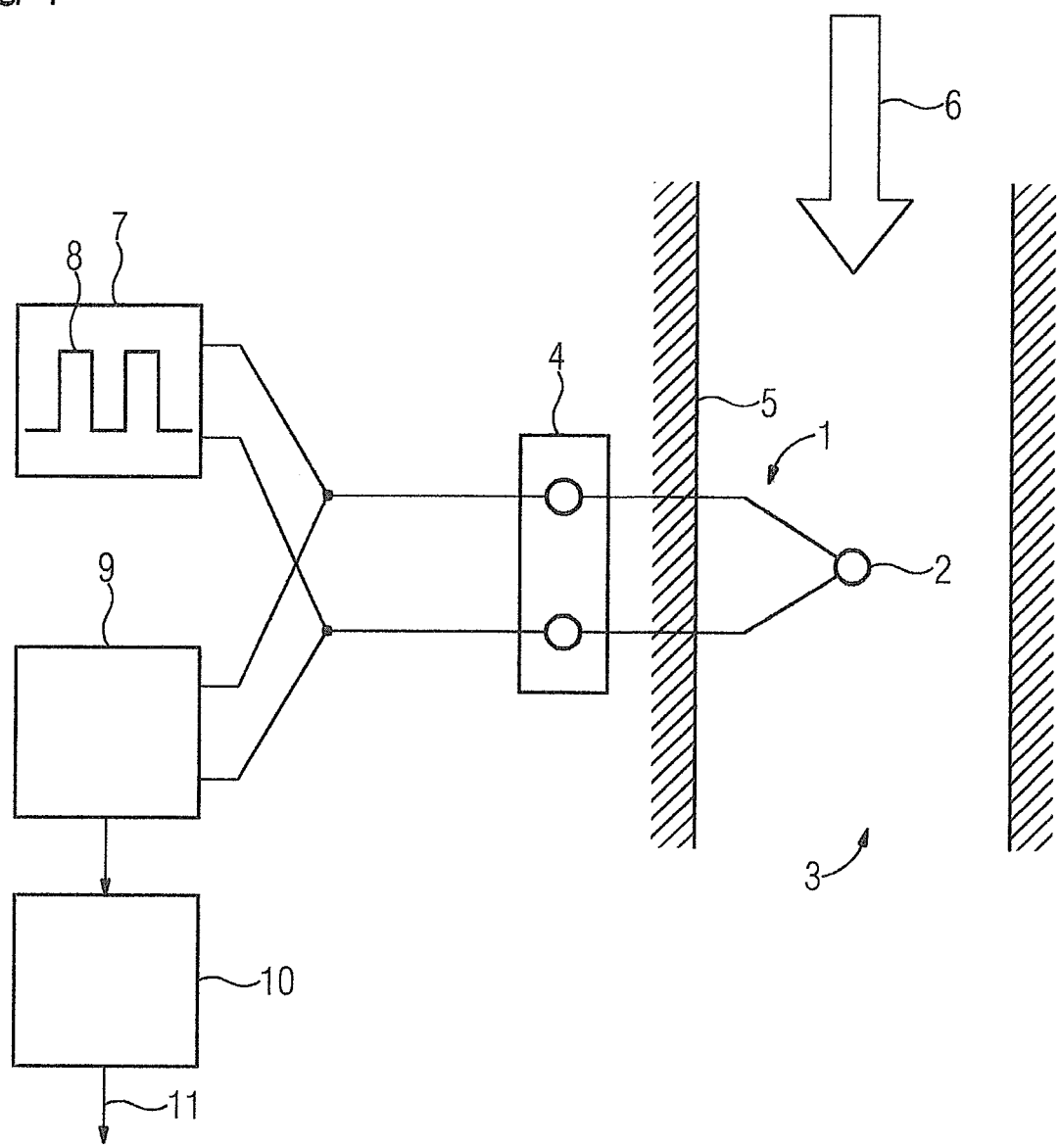
FIG. 1 is a schematic exemplary embodiment of the inventive gas analyzer.

FIG. 1 shows a schematic representation of a block diagram of a gas analyzer with a thermoelement probe 1, which is arranged in thermal contact with its measuring point 2 (in other words the hot connecting point) in the interior of the channel 3 and with its cold junction 4 (in other words the cold connecting point) in the region of the wall 5 of the channel 3. A ternary or multiple gas mixture 6, the composition of which is to be determined quantitatively, flows through the channel 43. The thermoelement probe 1 can be an individual thermoelement or a chain of thermoelements. The thermoelement probe 1 is connected with its cold connecting point 4 to a control device 7, which controls the thermoelement probe 1 with a series of current pulses 8. Furthermore, the thermoelement probe 1 is connected to a measuring device 9 which, in the pauses between the current pulses 8 at the cold junction 4, measures the electrical voltage generated by the thermoelement probe 1. Arranged downstream of the measuring device 9 is an evaluation device 10 that measures the temperature difference between the measuring point 2 and the wall 5 of the channel 3 from the voltage measured in the pauses between the current pulses 8 and calculates the ratio of these components therefrom and from known parameters such as in particular the specific heat conductivity of the components of the gas mixture to be measured 3 and outputs the same as a measured value 11.

Figure 2:
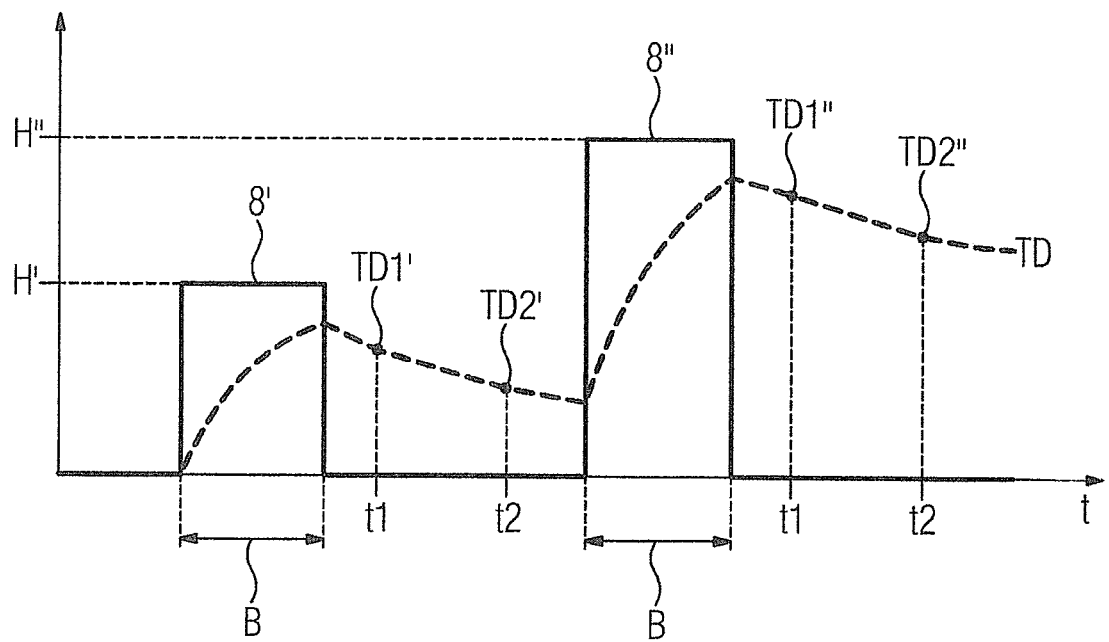
FIG. 2 is a graphical plot of a first exemplary embodiment for two current pulses with a different energy content in accordance with the invention.
Figure 3:
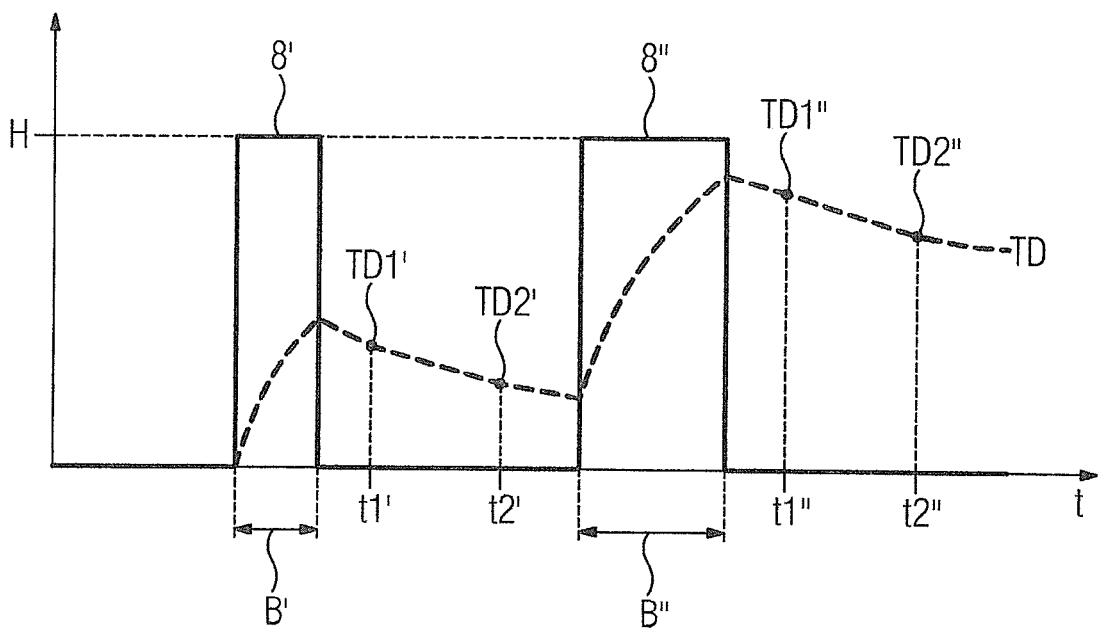
FIG. 3 is a graphical plot of a further exemplary embodiment for the two current pulses in accordance with the invention.

FIG. 2 shows an exemplary graphical plot of two current pulses 81 and 82 generated by the control device 7 with, in each case, a different energy content. In the example shown, the two current pulses 8' and 8" have different pulse heights (H', H") with the same width (duration) B. Furthermore, the course of the temperature difference TD between the measuring point 2 and the wall 5 of the channel 3 and the cold junction 4 is shown. Temperature difference values TD1', TD2' and TD1", TD2" are captured in each pause between two current pulses 8 at two different time instants t1 and t2. Each of the time instants t1, t1 lie at predetermined intervals at the end of the respectively preceding current pulse 8' or 8". The temperature difference value TD1' initially captured after the high-energy current pulse 8' is higher than the temperature difference value TD1" captured initially after the low-energy current pulse 8".

As FIG. 2 shows, the temperature difference values TD1', TD2', TD1", TD2" can be predetermined instead of the time intervals between the time instants t1, t2 at the respectively preceding current pulses 8' or 8', where the time instants t1', t2' and t1", t2" are then captured, during which the predetermined temperature difference values TD1 and TD2 are reached. Furthermore, FIG. 2 shows an alternative example of the two current pulses 8' and 8", which here have different widths B', B" with the same pulse height H.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas analyzer for a gas mixture with at least three components, comprising:
    a channel guiding the gas mixture;
    a thermoelement probe having a measuring point in an interior of the channel and a cold junction in thermal contact with a wall of the channel;
    a control device configured to induce pulsed activation of the thermoelement probe via current pulses;
    a measuring device configured to measure a voltage at the cold junction of the thermoelement probe in pauses between the current pulses; and an evaluation device configured to determine a temperature difference between the measuring point and the cold junction from the measured voltage and configured to calculate a ratio of the at least three components of the gas mixture from temperature difference values determined in each pause at at least two different time instants;

wherein the control device is further configured to generate current pulses with at least two different energy contents; and wherein the evaluation device is further configured to capture a higher temperature difference value in a pause after a current pulse with a higher energy content at a first time instant of the at least two different time instants and configured to utilize the captured higher temperature difference value for a calculation than after a current pulse with a lower energy content.

2. The gas analyzer as claimed in claim 1, wherein the control device is further configured to generate the current pulses with different energy contents via different pulse heights.

3. The gas analyzer as claimed in claim 2, wherein the control device is further configured to generate the current pulses with different energy contents via different pulse widths.

4. The gas analyzer as claimed in claim 2, wherein the evaluation device is further configured to determine time instants at which the temperature difference reaches at least two different predetermined temperature difference values, and further configured to utilize intervals between the determined time instants at an end of a respectively preceding current pulse to calculate the ratio of the components of the gas mixture.

5. The gas analyzer as claimed in claim 1, wherein the control device is further configured to generate the current pulses with different energy contents via different pulse widths.

6. The gas analyzer as claimed in claim 5, wherein the evaluation device is further configured to determine time instants at which the temperature difference reaches at least two different predetermined temperature difference values, and further configured to utilize intervals between the determined time instants at an end of a respectively preceding current pulse to calculate the ratio of the components of the gas mixture.

7. The gas analyzer as claimed in claim 1, wherein the evaluation device is further configured to fix the at least two different time instants to determine the temperature difference values at predetermined intervals at an end of a respectively preceding current pulse.

8. The gas analyzer as claimed in claim 1, wherein the evaluation device is further configured to determine time instants at which the temperature difference reaches at least two different predetermined temperature difference values, and further configured to utilize intervals between the determined time instants at an end of a respectively preceding current pulse to calculate the ratio of the components of the gas mixture.

* * * * *